(12) United States Patent
Cobb

(10) Patent No.: US 11,839,408 B2
(45) Date of Patent: Dec. 12, 2023

(54) SYSTEMS, DEVICES, AND METHODS FOR UTERINE HEMOSTASIS

(71) Applicant: Lucie Medical Inc, Spartanburg, SC (US)

(72) Inventor: Jennifer West Cobb, Spartanburg, SC (US)

(73) Assignee: Lucie Medical Inc., Spartanburg, SC (US)

( * ) Notice: Subject to any disclaimer, the term of this patent is extended or adjusted under 35 U.S.C. 154(b) by 0 days.

(21) Appl. No.: 18/185,311

(22) Filed: Mar. 16, 2023

(65) Prior Publication Data

US 2023/0320753 A1    Oct. 12, 2023

Related U.S. Application Data

(60) Provisional application No. 63/328,257, filed on Apr. 6, 2022.

(51) Int. Cl.
*A61B 17/42* (2006.01)
*A61B 17/12* (2006.01)
(Continued)

(52) U.S. Cl.
CPC .... *A61B 17/42* (2013.01); *A61B 2017/00849* (2013.01); *A61B 2017/00942* (2013.01);
(Continued)

(58) Field of Classification Search
CPC ........... A61M 1/84; A61M 1/87; A61B 17/42; A61B 2017/4216; A61B 2017/4225;
(Continued)

(56) References Cited

U.S. PATENT DOCUMENTS 9,550,014 B2   1/2017  Norred et al.
10,064,651 B2  9/2018  Norred et al.
(Continued)

OTHER PUBLICATIONS

Cebekhulu, S. N. et al. (2022), "Suction Tube Uterine Tamponade" for treatment of refractory postpartum hemorrhage: Internal feasibility and acceptability pilot of a randomized clinical trial. International Journal of Gynecology & Obstetrics, 158(1), 79-85. 7 pages.
(Continued)

*Primary Examiner* — Wade Miles
(74) *Attorney, Agent, or Firm* — Dority & Manning, P.A.

(57) ABSTRACT

A device may include a flexible tube comprising: a distal end, a proximal tip, the proximal tip comprising a suction line extension being configured for placement in a uterine cavity of a uterus after childbirth, a tube center of the flexible tube; and at least one lumen around the tube center, the at least one lumen comprising a suction line, the suction line being in communication with a source of negative pressure and the suction line extension, the suction line extension being configured for applying the negative pressure to the uterine cavity using the source of the negative pressure thereby causing mechanical hemostasis of bleeding blood vessels of a uterine wall of the uterine cavity. Embodiments include an anchoring mechanism being proximate to the suction line extension along the flexible tube, the anchoring mechanism being configured for maintaining the suction line extension in a desired position within the uterine cavity.

15 Claims, 10 Drawing Sheets

(51) Int. Cl.
*A61M 1/00* (2006.01)
*A61M 25/10* (2013.01)
*A61M 25/00* (2006.01)
*A61B 17/00* (2006.01)

(52) U.S. Cl.
CPC .............. *A61B 2017/12004* (2013.01); *A61B 2017/4216* (2013.01); *A61B 2217/005* (2013.01); *A61M 1/87* (2021.05); *A61M 25/007* (2013.01); *A61M 25/10* (2013.01)

(58) Field of Classification Search
CPC ........... A61B 2017/12004; A61B 2017/00849; A61B 2217/005
See application file for complete search history.

(56) References Cited

U.S. PATENT DOCUMENTS

| | | | |
|---|---|---|---|
| 10,820,926 B1* | 11/2020 | Leal | A61B 17/4241 |
| 11,241,254 B2 | 2/2022 | Norred et al. | |
| 11,291,473 B2 | 4/2022 | Norred et al. | |
| 11,517,336 B2 | 12/2022 | Bair et al. | |
| 2008/0045924 A1* | 2/2008 | Cox | A61B 17/42 604/515 |
| 2010/0274260 A1* | 10/2010 | D'Arpiany | A61B 17/4241 606/119 |
| 2014/0378750 A1* | 12/2014 | Buster | A61B 17/42 600/33 |
| 2014/0378752 A1* | 12/2014 | Buster | A61B 50/13 600/33 |
| 2014/0378754 A1* | 12/2014 | Buster | A61B 17/42 600/34 |
| 2015/0272622 A1* | 10/2015 | Carson | C12Q 1/6883 514/10.5 |
| 2017/0014218 A1* | 1/2017 | Kawaura | A61B 17/3403 |
| 2017/0224379 A1* | 8/2017 | Carson | A61K 31/568 |
| 2019/0282271 A1* | 9/2019 | Plessala | A61M 25/01 |
| 2021/0059739 A1* | 3/2021 | Holman | A61B 90/04 |
| 2022/0022916 A1* | 1/2022 | Uchida | A61B 17/12136 |
| 2022/0240982 A1* | 8/2022 | Norred | A61B 17/12131 |
| 2023/0075988 A1* | 3/2023 | Scheib | A61B 1/303 |
| 2023/0076736 A1* | 3/2023 | Scheib | A61G 13/101 |

OTHER PUBLICATIONS

Hofmeyr, G. J. et al. (2019). Randomized feasibility study of suction-tube uterine tamponade for postpartum hemorrhage. International Journal of Gynecology & Obstetrics, 146(3), 339-343. 10 pages.

Hofmeyr, G. J. et al. (2020). Novel suction tube uterine tamponade for treating intractable postpartum haemorrhage: description of technique and report of three cases. BJOG: An International Journal of Obstetrics & Gynaecology, 127(10), 1280-1283. 4 pages.

Haslinger, C. et al. (2021). Vacuum-induced tamponade for treatment of postpartum hemorrhage. Obstetrics and Gynecology, 138(3), 361. 5 pages.

Samartha Ram, H. et al. (2014). Vacuum retraction of uterus for the management of atonic postpartum hemorrhage. IOSR J Dent Med Sci (IOSR-JDMS), 2279-0853. 5 pages.

Panicker, T. N. Vasudeva. "Panicker's Vacuum Suction Haemostatic Device for Treating Post-Partum Haemorrhage", The Journal of Obstetrics and Gynecology of India (Mar.-Apr. 2017) 67(2):150-151, Mar. 1, 2017, 2 pages.

\* cited by examiner

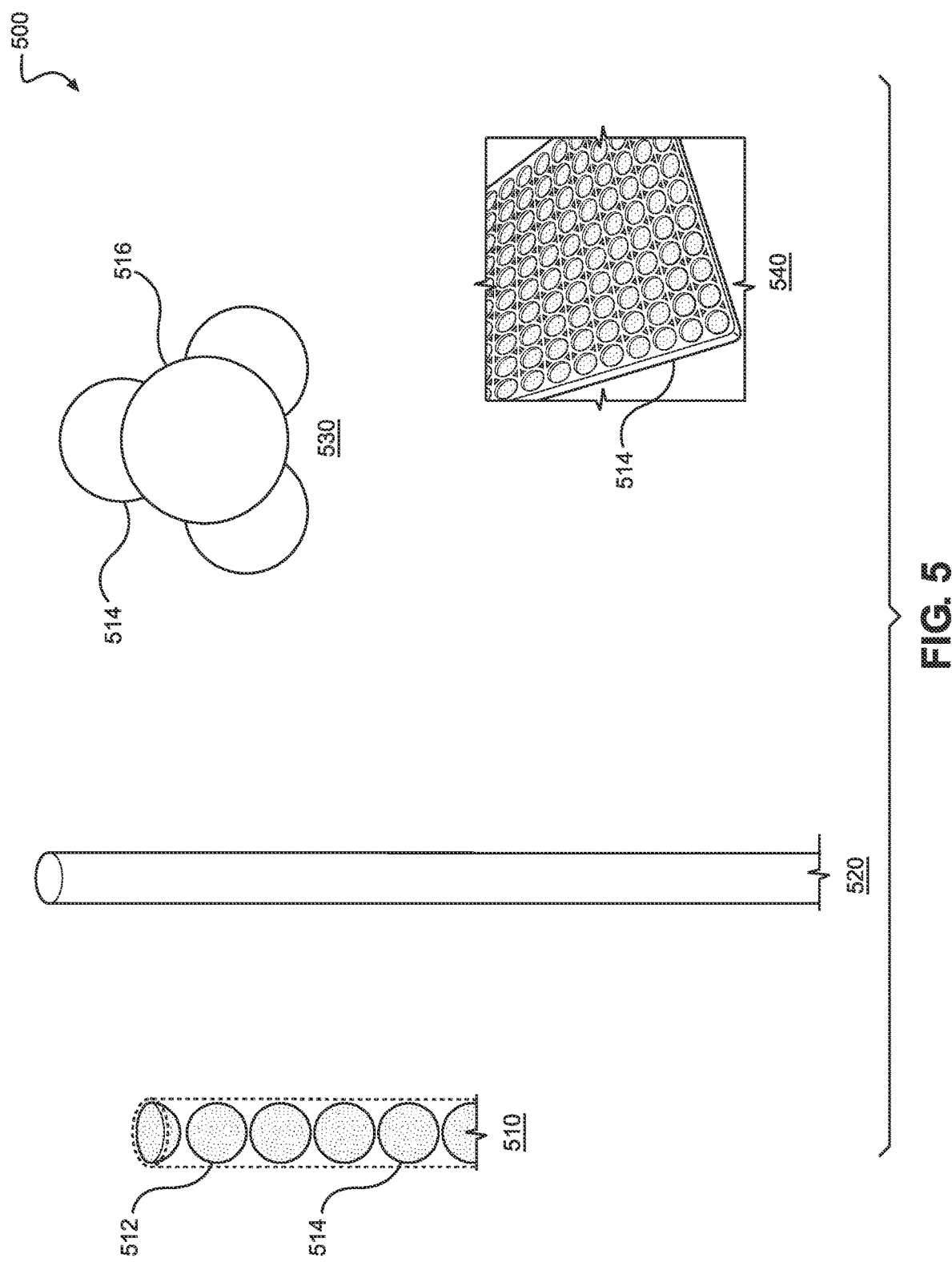

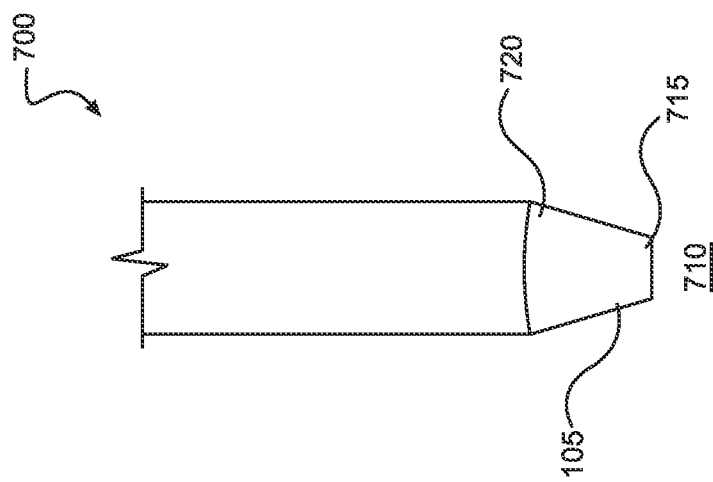

SYSTEMS, DEVICES, AND METHODS FOR UTERINE HEMOSTASIS

CROSS-REFERENCE TO RELATED APPLICATIONS

This patent application claims the priority and benefit of Provisional Patent Application Ser. No. 63/328,257, filed on Apr. 6, 2022. The aforementioned disclosure is hereby incorporated by reference including all references cited therein.

INVENTIVE FIELD

The present technology pertains to medical devices. The present technology, in particular, pertains to systems, devices, and methods for monitoring and controlling postpartum hemorrhage and excessive uterine bleeding.

SUMMARY

In some aspects, the techniques described herein relate to a postpartum hemorrhage mitigation device including: a flexible tube including: a distal end; a proximal tip, the proximal tip including a suction line extension being configured for placement in a uterine cavity of a uterus after childbirth either vaginally or via cesarean section; a tube center of the flexible tube; and at least one lumen around the tube center, the at least one lumen including a suction line, the suction line being in communication with a source of negative pressure and the suction line extension, the suction line extension being configured for applying the negative pressure to the uterine cavity using the source of the negative pressure thereby causing mechanical hemostasis of bleeding blood vessels of a uterine wall of the uterine cavity; and an anchoring mechanism being proximate to the suction line extension along the flexible tube, the anchoring mechanism being configured for maintaining the suction line extension in a desired position within the uterine cavity.

In some aspects, the techniques described herein relate to a postpartum hemorrhage mitigation device, wherein the suction line extension further includes one or more ports, the one or more ports being configured for drawing blood and other bodily fluids into the suction line extension from the bleeding blood vessels of the uterus.

In some aspects, the techniques described herein relate to a postpartum hemorrhage mitigation device, wherein at least one of the suction line extension and the suction line include volumetric indications, the volumetric indications being configured for measurement of a volume of blood within the suction line extension and the suction line for quantifying blood loss from the bleeding blood vessels of the uterus for a clinician to evaluate postpartum hemorrhaging.

In some aspects, the techniques described herein relate to a postpartum hemorrhage mitigation device, wherein the one or more ports include a plurality of ports, the plurality of ports including at least one of round pores, slits, and oval pores.

In some aspects, the techniques described herein relate to a postpartum hemorrhage mitigation device, wherein the one or more ports include both suction ports and protection pores, the protection pores protruding beyond an outer boundary of the flexible tube for protecting endometrium of the uterine wall from damage during suction.

In some aspects, the techniques described herein relate to a postpartum hemorrhage mitigation device, wherein the one or more ports include suction ports, the suction ports being positioned in a one-hundred-and-eighty-degree spiral configuration around the tube center.

In some aspects, the techniques described herein relate to a postpartum hemorrhage mitigation device, wherein the at least one lumen includes a plurality of lumens; and wherein the at least one lumen further includes a guidewire.

In some aspects, the techniques described herein relate to a postpartum hemorrhage mitigation device, wherein the guidewire includes a malleable plastic-coated metal rod placed inside the at least one lumen to reinforce the at least one lumen, the malleable plastic-coated metal rod being configured for aiding directing of the suction line towards the uterus.

In some aspects, the techniques described herein relate to a postpartum hemorrhage mitigation device, wherein the suction line includes a semi-flexible catheter.

In some aspects, the techniques described herein relate to a postpartum hemorrhage mitigation device, wherein the proximal tip of the flexible tube further includes a semi-ridged end, the semi-ridged end being configured for steerability and push-ability of the postpartum hemorrhage mitigation device.

In some aspects, the techniques described herein relate to a postpartum hemorrhage mitigation device, wherein the anchoring mechanism is a collapsible anchoring mechanism, the collapsible anchoring mechanism being configured for an open state when the collapsible anchoring mechanism is positioned within the uterine cavity and for a collapsed state during positioning of the postpartum hemorrhage mitigation device within the uterine cavity.

In some aspects, the techniques described herein relate to a postpartum hemorrhage mitigation device, wherein the anchoring mechanism is an inflatable anchoring mechanism, the inflatable anchoring mechanism being configured for an inflated state when the inflatable anchoring mechanism is positioned within the uterine cavity and in a deflated state during positioning of the postpartum hemorrhage mitigation device within the uterine cavity.

In some aspects, the techniques described herein relate to a postpartum hemorrhage mitigation device, wherein the suction line extension further includes a first wing and a second wing, the first wing and the second wing being in a proximate position along the flexible tube to the anchoring mechanism and being configured for maintaining a position of the suction line extension in the uterine cavity.

In some aspects, the techniques described herein relate to a postpartum hemorrhage mitigation device, further including an hourglass shaped placement marker, the hourglass shaped placement marker being configured for movement along the suction line for personalization of the postpartum hemorrhage mitigation device to a size of the uterus.

In some aspects, the techniques described herein relate to a postpartum hemorrhage mitigation device, wherein the hourglass shaped placement marker covers one or more ports.

In some aspects, the techniques described herein relate to a postpartum hemorrhage mitigation device, wherein the anchoring mechanism is a wavy placement anchor.

In some aspects, the techniques described herein relate to a postpartum hemorrhage mitigation device, wherein the flexible tube is tapered towards the distal end for positioning of the postpartum hemorrhage mitigation device within the uterine cavity.

In some aspects, the techniques described herein relate to a postpartum hemorrhage mitigation device, wherein the at least one lumen includes a hydrophilic coating, the hydrophilic coating providing compatibility with bodily fluids and reducing friction of the at least one lumen.

In some aspects, the techniques described herein relate to a postpartum hemorrhage mitigation device including: a flexible tube including: a distal end; a proximal tip, the proximal tip including a suction line extension being configured for placement in a uterine cavity of a uterus after childbirth either vaginally or via cesarean section, the suction line extension including one or more ports, the one or more ports being configured for drawing blood and other bodily fluids into the suction line extension from bleeding blood vessels of a uterine wall of the uterine cavity, the one or more ports including suction ports, the suction ports being positioned in a one-hundred-and-eighty-degree spiral configuration around a tube center of the flexible tube, the one-hundred-and-eighty-degree spiral configuration preventing blockage of all of the suction ports; wherein the suction line extension further includes volumetric indications, the volumetric indications being configured for measurement of a volume of blood within the suction line extension and the suction line for quantifying blood loss from the bleeding blood vessels for a clinician to evaluate postpartum hemorrhaging; and at least one lumen around the tube center, the at least one lumen including a suction line, the suction line being in communication with a source of negative pressure and the suction line extension, the suction line extension being configured for applying the negative pressure to the uterine cavity using the source of the negative pressure thereby causing mechanical hemostasis of the bleeding blood vessels of the uterine wall of the uterine cavity; and an anchoring mechanism being proximate to the suction line extension along the flexible tube, the anchoring mechanism being configured for maintaining the suction line extension in a desired position within the uterine cavity.

In some aspects, the techniques described herein relate to a postpartum hemorrhage mitigation device including: a flexible tube including: a distal end; a proximal tip, the proximal tip including a suction line extension being configured for placement in a uterine cavity of a uterus after childbirth either vaginally or via cesarean section, the suction line extension including one or more ports, the one or more ports being configured for drawing blood and other bodily fluids into the suction line extension from bleeding blood vessels of a uterine wall of the uterine cavity, the one or more ports including suction ports, the suction ports being positioned in a one-hundred-and-eighty-degree spiral configuration around a tube center of the flexible tube, the one-hundred-and-eighty-degree spiral configuration preventing blockage of all of the suction ports; and at least one lumen around the tube center, the at least one lumen including a suction line, the suction line being in communication with a source of negative pressure and the suction line extension, the suction line extension being configured for applying the negative pressure to the uterine cavity using the source of the negative pressure thereby causing mechanical hemostasis of the bleeding blood vessels of the uterine wall of the uterine cavity; and an anchoring mechanism being proximate to the suction line extension along the flexible tube, the anchoring mechanism being configured for maintaining the suction line extension in a desired position within the uterine cavity.

BACKGROUND

Postpartum hemorrhage (PPH) is the leading cause of maternal morbidity and mortality worldwide and is responsible for twenty-five percent of maternal deaths. Complications for PPH are also high with more than 1.5 million women annually experiencing morbidities. Literature states that the incidence and severity are increasing in both low-resourced and high-resourced settings. Uterine atony is the root cause of nearly eighty percent of PPH's and uterine atony is also the most preventable. Other less common causes include trauma, coagulopathy and retained tissue. After the placenta is delivered, the uterus must contract the fibers of the myometrium to control the bleeding. If the uterus remains atonic, the vessels are unable to constrict causing hemorrhage.

Postpartum hemorrhage is a condition that occurs when a woman's uterus bleeds more than 500 mL of blood within 24 hours following vaginal childbirth or 1000 mL of blood within twenty-four hours following cesarean childbirth. Often, the condition is caused when the woman's uterus fails to contract postpartum, which leaves blood vessels within the uterus open, so they continue to bleed. Postpartum hemorrhage may lead to a significant loss of blood from, and in extreme cases death of the woman.

Traditionally, it is difficult to diagnose and/or determine the amount of postpartum hemorrhage because it is difficult to determine or measure the volume of postpartum blood-loss, as there are inadequate means to capture the blood and accurately measure it. This is further complicated by blood pooling in the uterine cavity over time. This pooled blood may be held in place via, for example, a blood clot that forms at the base of the uterus and covers the opening to the cervical canal so that the woman may be bleeding internally (occult blood loss) with no vaginal bleeding to alert medical staff that postpartum hemorrhage may be occurring.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. The present technology is illustrated by way of example, and not limitation, in the figures of the accompanying drawings in which:

FIG. 5 is an illustration of exemplary postpartum hemorrhage mitigation devices before being positioned within a uterine cavity, in accordance with some embodiments of the present technology.

FIG. 7 is an illustration of an exemplary postpartum hemorrhage mitigation device before being positioned within a uterine cavity including a tapered tip to attach to the suction line, in accordance with some embodiments of the present technology.

Figure 1:
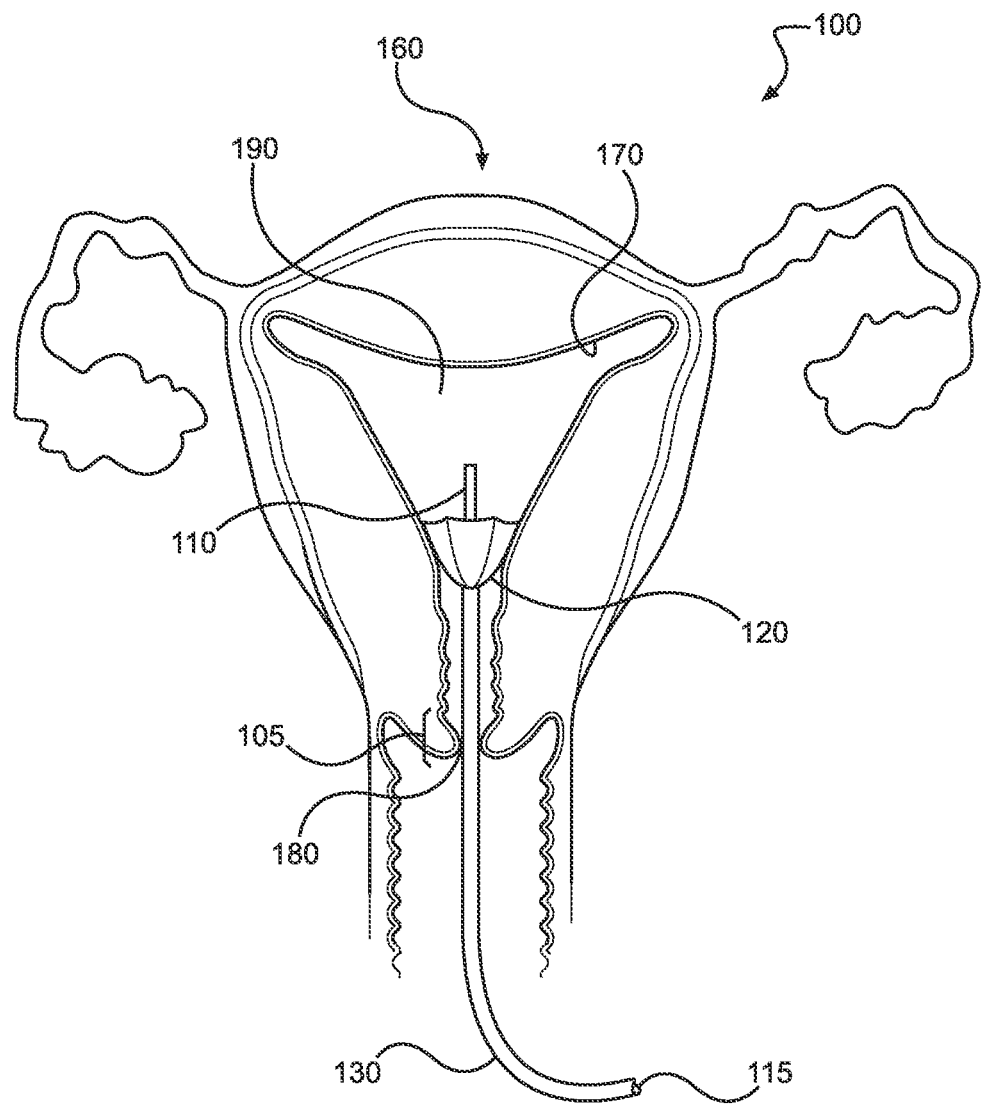
FIG. 1 is an illustration of a first exemplary postpartum hemorrhage mitigation device positioned within a mammal's uterus, in accordance with some embodiments of the present technology.

Throughout the drawings, the same reference numerals, and characters, unless otherwise stated, are used to denote like features, elements, components, or portions of the illustrated embodiments. Moreover, while the subject technology will now be described in detail with reference to the drawings, the description is done in connection with the illustrative embodiments. It is intended that changes and modifications can be made to the described embodiments without departing from the true scope and spirit of the present technology as defined by the appended claims.

DETAILED DESCRIPTION

Embodiments of the present disclosure are directed to postpartum hemorrhage mitigation devices as described herein. For example, embodiments include postpartum hemorrhage mitigation devices for contraction of a uterus, restoration of uterine tone, maintenance of uterine tone, and hemostasis of blood vessels within the uterus. Cesarean sections are the most common surgery performed each year. It is expected that by 2030, there will be thirty-eight million surgeries per year, worldwide. Cesarean sections are an independent risk factor for Postpartum hemorrhage (PPH) and sepsis.

In various embodiments postpartum hemorrhage mitigation devices of the present technology use negative pressure wound therapy. For example, negative pressure wound therapy is an innovative procedure used both on the skin surface and in endoscopic procedures. Furthermore, negative pressure wound therapy is used to provide local debridement, reduce bacterial contamination, drain wound secretions, reduce local edema and stimulate the froth of granulation tissue. Worldwide, sepsis episodes are one of the five most common causes of death associated with childbirth. Although rare, peritonitis can cause cesarean section scar dehiscence. Moreover, a history of cesarean sections and uterine surgery increases the risk of dehiscence.

Traditionally, postpartum blood loss is estimated by clinicians via visual observation of absorbent materials positioned near a pregnant mammal such as menstrual pads and bed sheets. These visual observations often underestimate the volume of blood loss by thirty-three percent to fifty percent, particularly when large amounts of blood are lost. The inaccuracy of visual observations is further exacerbated by the fact that pregnant mammals excrete fluids other than blood (e.g., urine, irrigation fluid, and/or amniotic fluid) during labor, delivery, and postpartum recovery, which may make it difficult to visually assess how much blood (as opposed to other fluids) may have been lost. The present technology solves these problems by providing a way to quantify postpartum blood loss through evacuation of blood directly from the uterus before the blood may be contaminated with other fluids.

Various embodiments of the present technology are directed to postpartum hemorrhage mitigation devices for treatment of postpartum hemorrhage (PPH) and the prevention of PPH. For example, the postpartum hemorrhage mitigation devices of the present technology decrease uterine bleeding both in obstetric and gynecologic cases and treat uterine wounds with negative pressure (i.e., wound therapy) including the hysterotomy incision (i.e., C/S incision) and accreta (uterine defects).

Embodiments of the present technology are directed to postpartum hemorrhage mitigation devices including monitoring and diagnosing postpartum hemorrhage (PPH) by qualification of real-time blood loss from the uterus. Embodiments include treating or preventing local infection control. Embodiments further include clot extraction. For example, a postpartum hemorrhage mitigation device may be placed vaginally when clots cannot be expressed manually. For example, this may be important during minimally or not dilated cervices such as during a planned cesarean section.

In some embodiments, postpartum hemorrhage mitigation devices of the present technology include single or multiple lumens, a flexible tube with a semi-ridged end for steerability and push-ability, a guidewire or stylet for proper positioning, oval pores and/or slits and/or round pores, a positioning ring at the cervical external orifice, a hydrophilic coating (e.g., polymer) on the inside of the catheter, and markings on the end of the tube (e.g., external of the vagina) for quantification of blood loss. In some embodiments a stylet is a single straight wire with a hub at one end which is inserted into the catheter prior to placement. The stylet may be used to add stiffness to the catheter during insertion and the stylet may be manually adjusted by a clinician to be curved for ease of placement. After placement, the stylet may be removed from the catheter. In some embodiments a guide wire is a thin wire used to guide the placement of postpartum hemorrhage mitigation devices of the present technology.

In various embodiments the present technology is directed to postpartum hemorrhage mitigation devices configured to monitor and quantitatively measure postpartum blood loss after cesarean delivery and prevent postpartum hemorrhage by, for example, mechanical, vacuum-induced tamponade that may encourage contraction of the uterus, restoration of uterine tone, maintenance of uterine tone, and/or hemostasis of the blood vessels within the uterus. In some embodiments, the devices disclosed herein may configured to be positioned within the uterus of mammals (e.g., human women) who have recently undergone childbirth via, for example, a cesarean section and apply negative pressure to the uterus to assist with contraction of the uterus. This contraction of the uterus acts to close uterine blood vessels and/or reduce bleeding from uterine blood vessels thereby controlling risks associated with postpartum hemorrhage. The negative pressure may be applied to the uterus via, for example, a vacuum pump and/or a standard suction cannister that may be coupled to a wall-regulated suction of a hospital room. Exemplary amounts of negative pressure applied to the postpartum hemorrhage mitigation devices disclosed herein range from 50-300 mmHg depending on, for example, a duration of time following childbirth that the negative pressure is applied. For example, an initially high negative pressure (e.g., 150-300 mmHg) may be applied to the uterine cavity between five and ten minutes following placement of the postpartum hemorrhage mitigation device disclosed herein to maximize the initial uterine contraction/restoration of uterine tone. The amount of negative pressure may then be gradually reduced over time to assist with, for example, continued contraction of the uterus, maintenance of uterine tone, and/or evacuation of blood from the uterine cavity following the initial contraction of the uterus.

The postpartum hemorrhage mitigation device disclosed herein may also be configured to draw blood away from the uterine cavity into a collection vessel so that a volume of blood the mammal is losing can be quantified in order to, for example, diagnose postpartum hemorrhage and/or determine when it is advisable to remove the device from the mammal's uterus because bleeding has been sufficiently reduced.

In various embodiments, the postpartum hemorrhage mitigation devices disclosed herein may be placed within a mammal's uterus via a surgical opening caused by a hysterotomy during cesarean delivery of her child and following delivery of the baby and placenta. The postpartum hemorrhage mitigation devices disclosed herein may be configured to be placed within the lower-uterine segment and, following placement of the postpartum hemorrhage mitigation device, a suction line (e.g., semi-flexible catheter) may be fed through the cervix and out the vagina for coupling to an external vacuum source. Then, the surgical opening may be closed, sealing a postpartum hemorrhage mitigation device within the uterus. Next, a cervical seal may be created via, for example, a diaphragm that covers the cervical opening and/or an inflatable balloon that occludes the cervical opening upon inflation. Once the seal is created, negative pressure may be applied to the suction line via the vacuum source and this negative pressure may contract the uterus and evacuate blood from the uterine cavity for quantification. Finally, the postpartum hemorrhage mitigation device may be extracted from the uterus via the cervix and vagina typically one to twenty-four hours following closure of the surgical opening when, for example attending clinical staff determines that the patient is no longer at risk for postpartum hemorrhage.

Turning now to the figures, FIG. 1 is an illustration of an exemplary postpartum hemorrhage mitigation device 100 positioned within a uterine cavity 190 bounded by a uterine wall 170 of a uterus 160 of a mammal (e.g., human woman, horse, dog, etc.) that recently gave birth via cesarean section. Postpartum hemorrhage mitigation device 100 includes a suction line extension 110, an anchoring mechanism 120, and a suction line 130. In various embodiments the suction line 130 may include a guidewire. The guidewire may be used to guide the anchoring mechanism 120, and the suction line 130 of the postpartum hemorrhage mitigation device 100 into place during insertion of the postpartum hemorrhage mitigation device 100 within the uterine cavity 190. In some embodiments, the postpartum hemorrhage mitigation device 100 includes a guidewire and the purpose of the guidewire is to properly position the postpartum hemorrhage mitigation device 100 using a minimally invasive technique.

Figure 10:
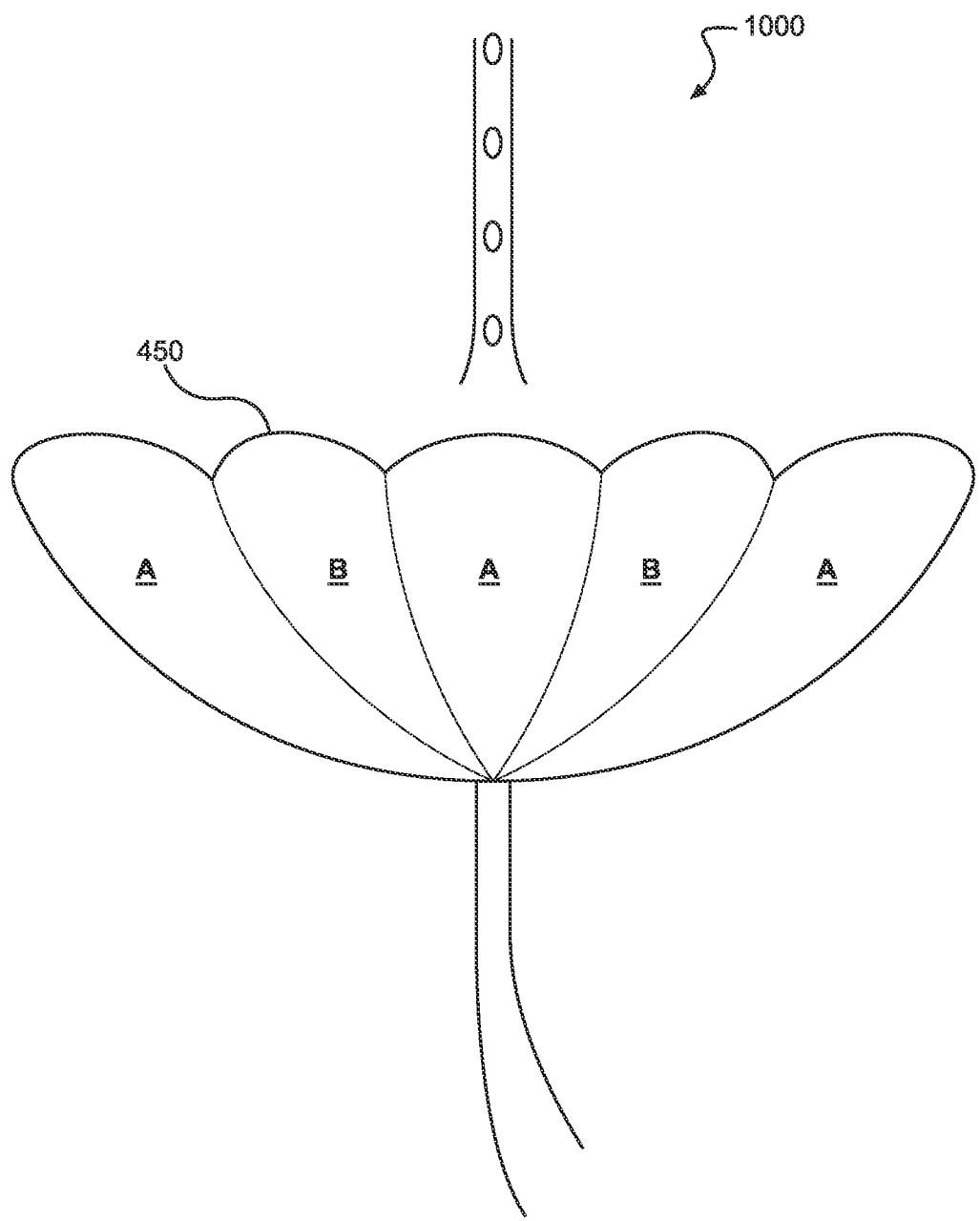
FIG. 10 is an illustration of an exemplary collapsible anchoring mechanism for a postpartum hemorrhage mitigation device within the uterus, in accordance with some embodiments of the present technology.

In some embodiments, the postpartum hemorrhage mitigation device 100 includes a flexible tube (not shown) comprising: a distal end 115; a proximal tip 105, the proximal tip 105 comprising a suction line extension 110 being configured for placement in the uterine cavity 190 of the uterus 160 after childbirth; a tube center (not shown) of the flexible tube; and at least one lumen (not shown) around the tube center, the at least one lumen comprising a suction line 130, the suction line 130 being in communication with a source of negative pressure (not shown) and the suction line extension 110, the suction line extension 110 being configured for applying the negative pressure to the uterine cavity 190 using the source of the negative pressure thereby causing mechanical hemostasis of bleeding blood vessels (not shown) of a uterine wall 170 of the uterine cavity 190; and the anchoring mechanism 120 being proximate to the suction line extension 110 along the flexible tube, the anchoring mechanism 120 being configured for maintaining the suction line extension 110 in a desired position within the uterine cavity 190. For example, the anchoring mechanism 120 may be a collapsible anchoring mechanism 450. Furthermore, the exemplary collapsible anchoring mechanism 450 is shown in FIG. 10 including a plurality of wings.

In various embodiments, the suction line 130 may be configured to couple to a source of negative pressure, such as a vacuum pump (not shown) so that negative pressure may be applied to the suction line 130. The suction line 130 is configured to be in communication with the suction line extension 110 and negative pressure applied to the suction line 130 may be communicated to the suction line extension 110 so that suction line extension 110 may apply negative pressure to the uterine cavity 190 via one or more ports (which may be embodied as holes) positioned within the suction line extension 110. In many embodiments, multiple ports (e.g., four ports to ten ports) may be used to, for example, distribute force attributable to the negative pressure over a particular surface area and/or maintain functioning of the device if one or more of the ports becomes occluded by, for example, a blood clot. Application of negative pressure via the port(s) in the suction line extension 110 may facilitate the application of negative pressure to the inner surface of uterine wall 170, thereby contracting the inner surface area uterine wall 170 and thereby causing mechanical hemostasis of potentially bleeding blood vessels positioned within the uterine wall 170. The ports in the suction line extension 110 may also be configured to draw blood and other bodily fluids into the suction line extension 110 so that they may be evacuated away from the uterine cavity 190 via the suction line 130. In some embodiments, the suction line 130 may be coupled to a collection vessel (e.g., jar or bag) configured to collect the fluids evacuated from the uterine cavity 190 so that a quantity of fluid/blood evacuated from the uterine cavity 190 may be measured. Additionally, or alternatively, the suction line 130 may have volumetric indications (e.g., in ten mL, twenty mL, or fifty mL increments) printed or stamped thereon so that a clinician may measure a volume of blood within the suction line 130. This measurement may be used to quantify blood loss and/or evaluate the mammal's risk of postpartum hemorrhage and/or the severity thereof.

In various embodiments, the anchoring mechanism 120 may be configured to assist with maintaining the suction line extension 110 in a desired position within the uterine cavity 190. Often times, the desired position for the suction line extension 110 is at the base of uterine cavity 190 directly above cervical canal 180 so that the suction line 130 extends from a base of the anchoring mechanism 120 through the cervical canal 180 and out of the mammal's body via the vagina to be coupled to the vacuum pump and/or collection receptacle. The guidewire may be used to properly position the anchoring mechanism 120 using a minimally invasive technique. The anchoring mechanism 120 may be made from a soft, flexible, material such as silicon and/or plastic and, some occasions, the anchoring mechanism 120 may open or otherwise spread apart to cover the cervical opening after being properly place into position. In some embodiments, suction line extension 110 may be configured with a port positioned proximate to anchoring mechanism 120 to evacuate any bodily fluids that may accumulate within the anchoring mechanism 120. In some embodiments, the at least one lumen comprises a plurality of lumens; and wherein the at least one lumen further comprises a guidewire (now shown).

In some embodiments, the postpartum hemorrhage mitigation device 100 is placed within the uterus 160 of a human woman, with the suction line 130 extending through the cervical canal 180 following a cesarean delivery of her child while the abdomen and the uterus 160 are surgically open. The anchoring mechanism 120 may be configured to enable extraction of the postpartum hemorrhage mitigation device 100 from uterine cavity 190 via pulling on the suction line 130 so that the anchoring mechanism 120 collapses enough to allow passage of the anchoring mechanism 120 and the suction line extension 110 through the cervical canal 180 and the vagina (not shown) and eventually to be extracted from the mammal's body.

Figure 2A:
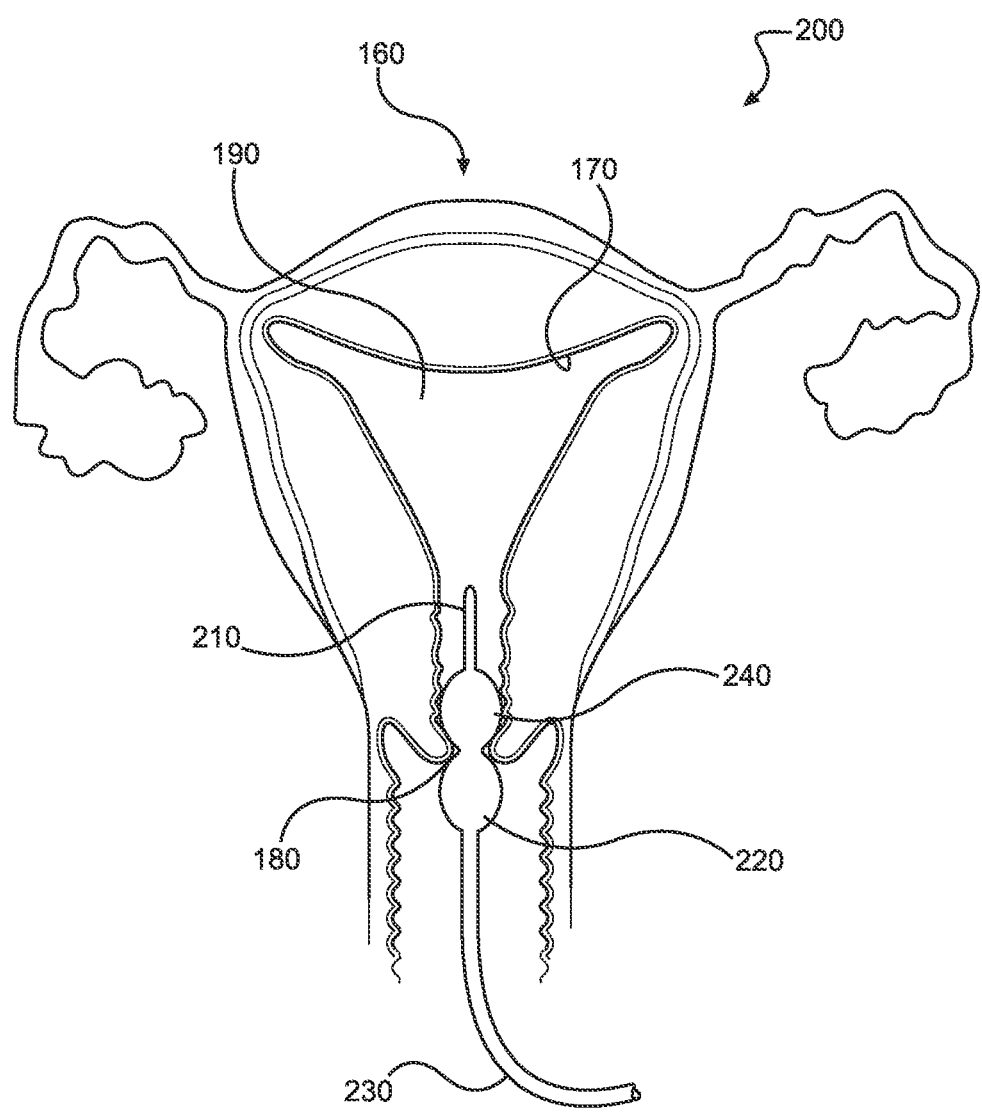
FIG. 2A is an illustration of a second exemplary postpartum hemorrhage mitigation device in an inflated state and positioned within a uterine cavity and cervical canal of a mammal who recently gave birth either vaginally or via cesarean section, in accordance with some embodiments of the present technology.
Figure 2B:
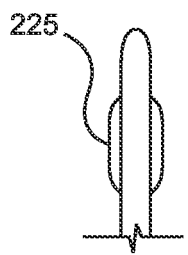
FIG. 2B is an illustration of a second postpartum hemorrhage mitigation device of FIG. 2A with the inflatable anchoring mechanism in a deflated state, in accordance with some embodiments of the present technology.

FIG. 2A is an illustration of a second exemplary postpartum hemorrhage mitigation device 200 with an inflatable anchoring mechanism in an inflated state and positioned within the uterine cavity 190 and the cervical canal 180 of a mammal who recently gave birth either vaginally or via cesarean section according to various embodiments. FIG. 2B is an illustration of the second postpartum hemorrhage mitigation device 200 with the inflatable anchoring mechanism 220 in a deflated state 225 prior to insertion into the uterus 160 according to some embodiments. The postpartum hemorrhage mitigation device 200 operates in a manner similar to the postpartum hemorrhage mitigation device 100 with the exception of the anchoring mechanism 120 of FIG. 1 may be an inflatable anchoring mechanism 220 (e.g., inflatable anchoring mechanism 220 in an inflated state is shown in FIG. 2A and the inflatable anchoring mechanism 220 in a deflated state 225 prior to insertion into the uterus 160 is shown in FIG. 2B). Postpartum hemorrhage mitigation device 200 includes a suction line extension 210, the inflatable anchoring mechanism 220, and a suction line 230. Prior to insertion into the uterus 160, the inflatable anchoring mechanism 220 (e.g., inflatable anchoring mechanism 220 in an inflated state is shown in FIG. 2A and the inflatable anchoring mechanism 220 in a deflated state 225 prior to insertion into the uterus 160 is shown in FIG. 2B) may be in a deflated state 225 as shown in FIG. 2B. The inflatable anchoring mechanism 220 in a deflated state 225 as shown in FIG. 2B may be inserted into cervical canal 180 either vaginally or via a surgical opening caused by a cesarean delivery of the mammal's baby or babies. Once placed within cervical canal 180, the inflatable anchoring mechanism 220 may be inflated to a degree sufficient to hold second exemplary postpartum hemorrhage mitigation device 200 and/or the inflatable anchoring mechanism 220 in a desired position within the uterine cavity 190 and/or the cervical canal 180. Additionally, or alternatively, the inflatable anchoring mechanism 220 may be inflated via insertion/injection of a fluid into the inflatable anchoring mechanism 220 via a port 240 positioned on the uterine-facing side of the inflatable anchoring mechanism 220 prior to surgically closing the uterus 160. The port 240 may be, for example, a one- or two-direction valve in various embodiments. The inflatable anchoring mechanism 220 may also be configured to seal the cervical canal 180 so that blood and other bodily fluids do not escape from the cervical cavity.

In various embodiments, the suction line 230 may be configured to inflate/deflate the inflatable anchoring mechanism 220 and/or communicate negative pressure to the suction line extension 210 via one or more ports positioned therein. The ports of suction line extension 210 may also be configured to evacuate blood and other bodily fluids from the uterine cavity 190 in a manner similar to the ports of the suction line extension 110.

In some embodiments, the inflatable anchoring mechanism 220 is configured for an inflated state when the inflatable anchoring mechanism 220 is positioned within the uterine cavity 190 and in a deflated state during positioning of the postpartum hemorrhage mitigation device 200 within the uterine cavity 190.

In some embodiments, the suction line 230 may have two lumens; a first lumen configured as an inflation line lumen for inflating and deflating the inflatable anchoring mechanism 220 and a second lumen configured as a suction line similar to suction line 130. The inflation line lumen may be configured to couple with an air and/or liquid source (not shown) that may be used to provide air/liquid used to inflate the inflatable anchoring mechanism 220.

In various embodiments, the postpartum hemorrhage mitigation device 200 is placed within the uterus 160 of a mammal, with the suction line extension 210 extending through the cervical canal 180 following a cesarean delivery of her child while the abdomen and uterus 160 are surgically open. Alternatively, postpartum hemorrhage mitigation device 200 may be inserted into cervical canal 180 and uterine cavity 190 via a vaginal route. Prior to extraction of postpartum hemorrhage mitigation device 200 from cervical canal 180, the inflatable anchoring mechanism 220 may be deflated enough to enable extraction of the postpartum hemorrhage mitigation device 200 from the uterine cavity 190 via pulling on the suction line 230 to allow passage of postpartum hemorrhage mitigation device 200 through the cervical canal 180 and the vagina (not shown) and eventual extraction from the mammal's body.

Figure 3:
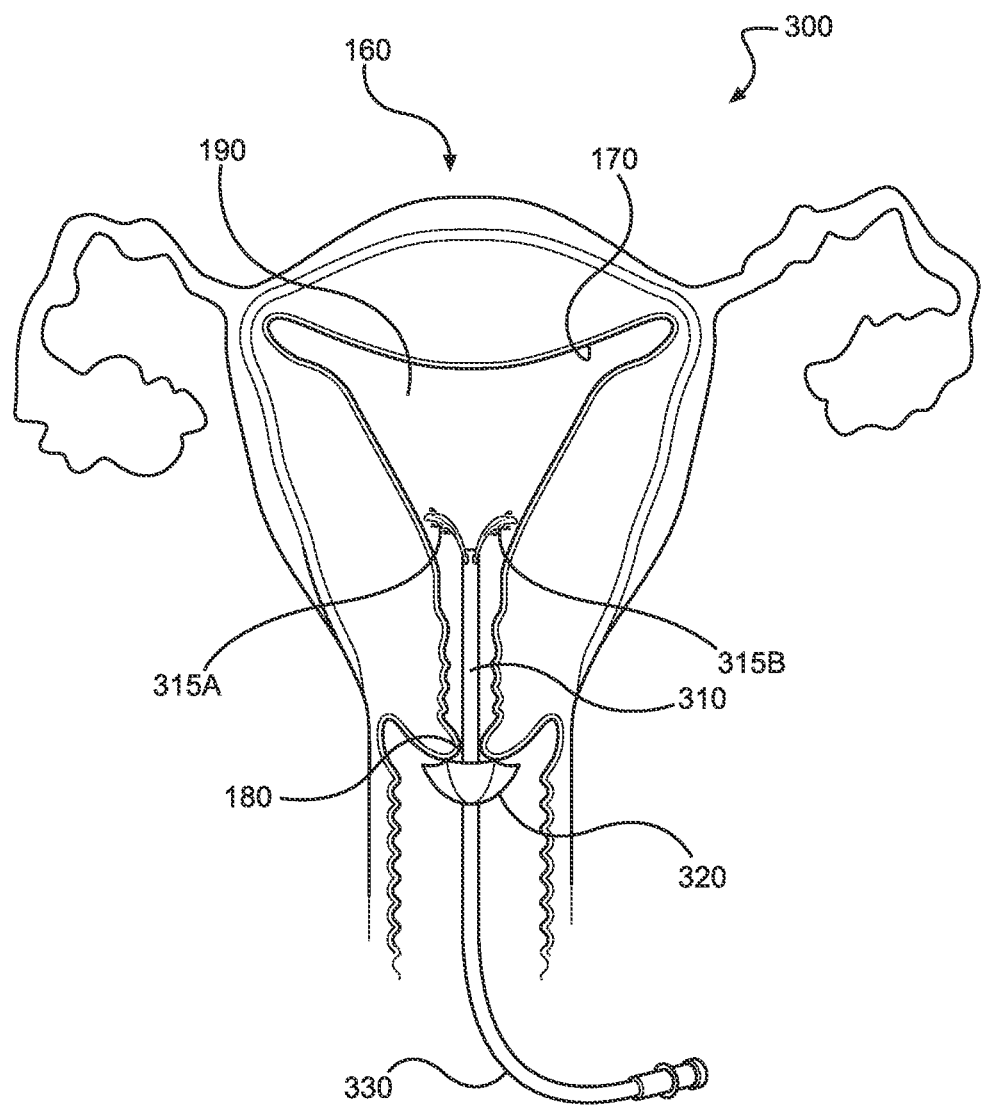
FIG. 3 is an illustration of a third exemplary postpartum hemorrhage mitigation device positioned within a uterine cavity and cervical canal of a mammal who recently gave birth either vaginally or via cesarean section, in accordance with some embodiments of the present technology.

According to various embodiments, FIG. 3 is an illustration of a third exemplary postpartum hemorrhage mitigation device 300 positioned within uterine cavity 190 and cervical canal 180 of a mammal who recently gave birth either vaginally or via cesarean section. Postpartum hemorrhage mitigation device 300 includes a suction line 330, an anchoring mechanism 320, a suction line extension 310, a first wing 315A and a second wing 315B.

In some embodiments, the postpartum hemorrhage mitigation device 300 operates in a manner similar to the postpartum hemorrhage mitigation device 100 with the exception that the anchoring mechanism 320 is positioned on the vaginal side of the cervical canal 180 (as opposed to the uterine side as shown by the anchoring mechanism 120 in FIG. 1) and suction line extension 310 includes a first wing 315A and a second wing 315B. The suction line extension 310, the first wing 315A, and/or the second wing 315B may include one or more ports configured to evacuate blood and other bodily fluids from the uterine cavity 190 in a manner similar to the ports of the suction line extension 110 and the suction line extension 210.

In some embodiments, the postpartum hemorrhage mitigation device 300 is placed within the uterus of a mammal, with the suction line 130 extending through cervical canal 180 following a cesarean delivery of her child while the abdomen and the uterus 160 are surgically open. Alternatively, the postpartum hemorrhage mitigation device 300 may be inserted into the cervical canal 180 via a vaginal route. The first wing 315A and the second wing 315B and/or the anchoring mechanism 320 may be configured to enable extraction of the postpartum hemorrhage mitigation device 300 from uterine cavity 190 via pulling on the suction line 330 so that first wing 315A and the second wing 315B and/or the anchoring mechanism 320 collapse enough to allow passage thereof through the cervical canal and the vagina (not shown) and eventually extracted from the mammal's body.

In some cases, the postpartum hemorrhage mitigation device(s) disclosed herein may be configured to be radio opaque and/or observable via fluoroscopy imaging techniques during a uterine artery embolization and also observable using ultrasound.

Additionally, or alternatively, a suction line may have a bifurcated lumen with, for example, a diaphragm or membrane running along the length that divides the lumen into two or more sub-lumens.

Figure 4:
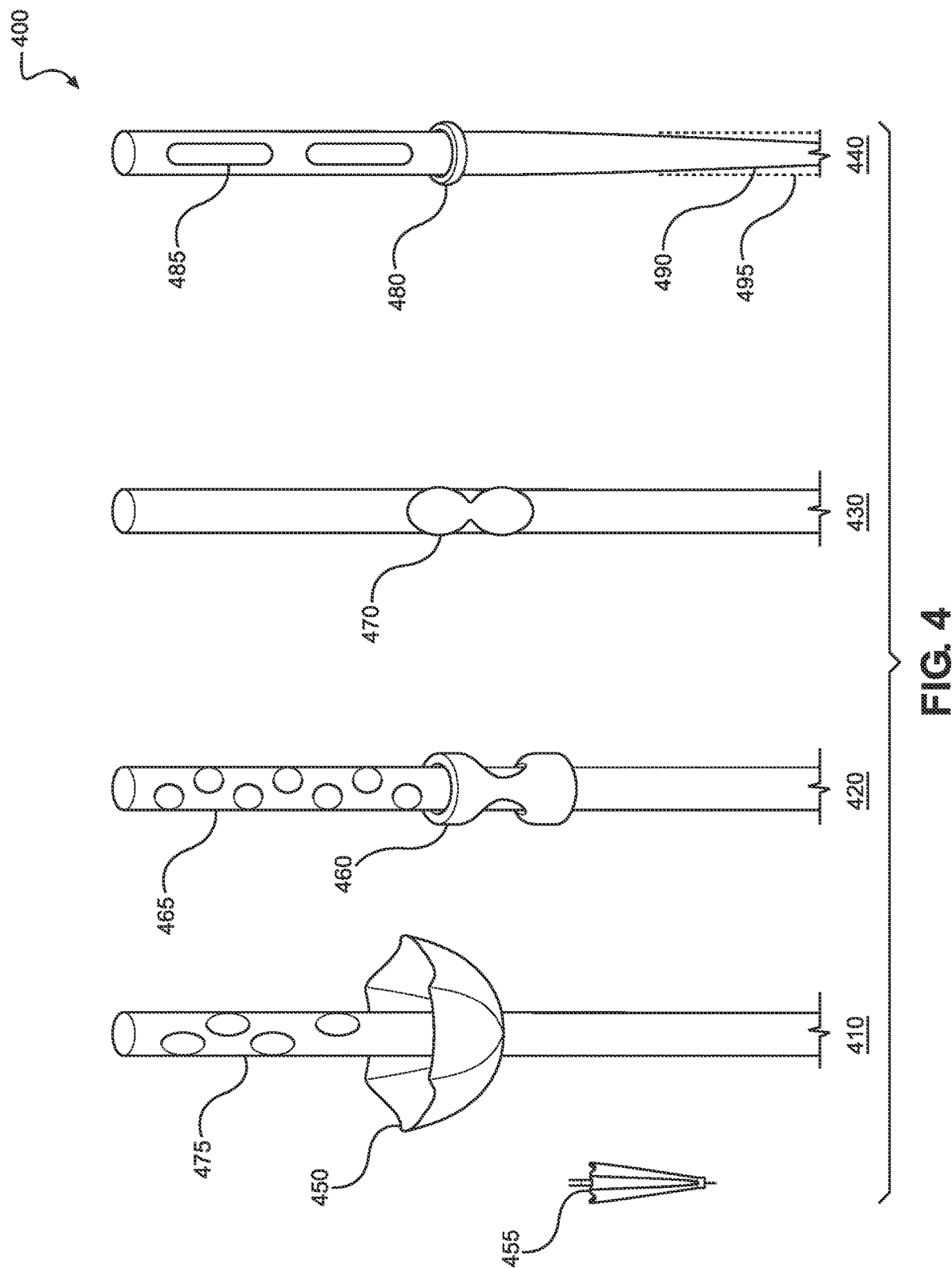
FIG. 4 is an illustration of exemplary postpartum hemorrhage mitigation devices before being positioned within a uterine cavity, in accordance with some embodiments of the present technology.

FIG. 4 is an illustration 400 of exemplary postpartum hemorrhage mitigation devices before being positioned within a uterine cavity, in accordance with some embodiments of the present technology. FIG. 4 illustrates various exemplary postpartum hemorrhage mitigation devices including a postpartum hemorrhage mitigation device 410, a postpartum hemorrhage mitigation device 420, a postpartum hemorrhage mitigation device 430, and a postpartum hemorrhage mitigation device 440. According to various embodiments, the postpartum hemorrhage mitigation device 410 includes a collapsible anchoring mechanism 450 shown in the open configuration in the postpartum hemorrhage mitigation device 410. In some instances, for example during insertion of the postpartum hemorrhage mitigation device 410 into the uterus, the collapsible anchoring mechanism 450 may be in the collapsed configuration 455. For example, the postpartum hemorrhage mitigation device 410 may comprise the anchoring mechanism being a collapsible anchoring mechanism 450, the collapsible anchoring mechanism being configured for an open state when the collapsible anchoring mechanism 450 is positioned within the uterine cavity 190 and for a collapsed state (e.g., collapsible anchoring mechanism 450) during positioning of the postpartum hemorrhage mitigation device 410 within the uterine cavity 190.

In some embodiments the collapsible anchoring mechanism 450 is an umbrella configuration comprising a plurality of wings. For example, an exemplary collapsible anchoring mechanism 450 is shown in FIG. 10 including a plurality of wings in the umbrella configuration.

The postpartum hemorrhage mitigation device 420 includes an hourglass shaped placement marker 460, which may slide up and cover ports (e.g., round pores 465 and/or slits 485 and/or oval pores 475) to allow the postpartum hemorrhage mitigation device 420 to be personalized and properly positioned to the size of a uterus. The ports may also be round pores 465 and/or slits 485 and/or oval pores 475 to allow for suction by connection to the suction line extension 110. In some embodiments, multiple ports (e.g., four ports to ten ports) may be used to, for example, distribute force attributable to the negative pressure over a particular surface area and/or maintain functioning of the device if one or more of the ports becomes occluded by, for example, a blood clot. Application of negative pressure via the ports in the suction line extension 110 may facilitate the application of negative pressure to the inner surface of uterine wall 170, thereby contracting the inner surface area uterine wall 170 and thereby causing mechanical hemostasis of potentially bleeding blood vessels positioned within the uterine wall 170. The ports in the suction line extension 110 (e.g., round ports 465) may also be configured to draw blood and other bodily fluids into the suction line extension 110 so that they may be evacuated away from the uterine cavity 190 via the suction line 130. FIG. 4 further illustrates the postpartum hemorrhage mitigation device 430 that includes a wavy placement anchor 470, which is variation of an anchoring mechanism (e.g., the anchoring mechanism 120 in FIG. 1). The postpartum hemorrhage mitigation device 440 includes a placement collar 480.

In some embodiments the at least one lumen comprises a plurality of lumens. For example, the postpartum hemorrhage mitigation device 440 shows a tapered inner lumen 490 and an outer lumen 495 with the outer lumen 495 having a consistent diameter adding thickness and push-ability of a catheter without using a stylet or guidewire. Furthermore, for example, postpartum hemorrhage mitigation device 440 shows ports (e.g., slits 485).

In some embodiments, the postpartum hemorrhage mitigation device 410 includes oval pores 475 and the postpartum hemorrhage mitigation device 420 includes round ports 465. For example, wherein the suction line extension further comprises one or more ports (e.g., round pores 465 and/or oval pores 475 and/or slits 485), the one or more ports (e.g., round ports 465 and oval pores 475) being configured for drawing blood and other bodily fluids into the suction line extension from the bleeding blood vessels of the uterus. For example, the postpartum hemorrhage mitigation device 410 includes ports comprising oval pores 475. For example, the postpartum hemorrhage mitigation device 420 includes round ports 465 a comprising round pores.

In some embodiments a problem in the field is having two rows of pores on each side of the flexible tube may be a problem because the postpartum uterine cavity (e.g., uterine cavity 190) may be a flat potential space with an anterior and posterior wall in apposition. If the two rows of pores could suck against the anterior and posterior walls, respectively, the two rows of pores may become obstructed leaving only a tip port for suction. Thus, it may be important to have pores facing in all directions so that in any position, some apertures would face laterally and would not be obstructed. A solution to this problem is that the pores may be positioned in one-hundred-and-eighty degree spirals rather than straight lines. For example, according to various embodiments the round ports 465 and the oval pores 475 may comprise suction ports, the suction ports being positioned in a one-hundred-and-eighty-degree spiral configuration around the tube center as shown by the round ports 465 and the oval pores 475.

FIG. 5 is an illustration 500 of exemplary postpartum hemorrhage mitigation devices before being positioned within a uterine cavity, in accordance with some embodiments of the present technology. FIG. 5 is an illustration 500 of various exemplary postpartum hemorrhage mitigation devices including a postpartum hemorrhage mitigation device 510, a postpartum hemorrhage mitigation device 520, a postpartum hemorrhage mitigation device 530, and protection pores 540 for a postpartum hemorrhage mitigation device. For example, postpartum hemorrhage mitigation device 510 shows ports (e.g., round ports 465 such as round pores and/or slits 485 and/or oval pores 475). The lighter shaded pores 512 may be suction pores to facilitate the application of negative pressure to the inner surface of uterine wall 170 and the darker shaded ports may be protection pores 514 may protrude beyond the outer boundaries of the postpartum hemorrhage mitigation device 510 to protect the endometrium from damage during suction. Furthermore, the postpartum hemorrhage mitigation device 530 illustrates a top down view of a catheter showing a plurality of projections. For example, two, three or four projections that may be pores that show protection pores 514 that protrude beyond the outer boundaries of the postpartum hemorrhage mitigation device 530. For example, protection pores 540 for a postpartum hemorrhage mitigation device. In some instances the postpartum hemorrhage mitigation device 530 includes the one or more ports comprise both suction ports and protection pores 514, the protection pores 514 protruding beyond an outer boundary of the flexible tube 516 for protecting endometrium of the uterine wall (not shown) from damage during suction.

Figure 6B:
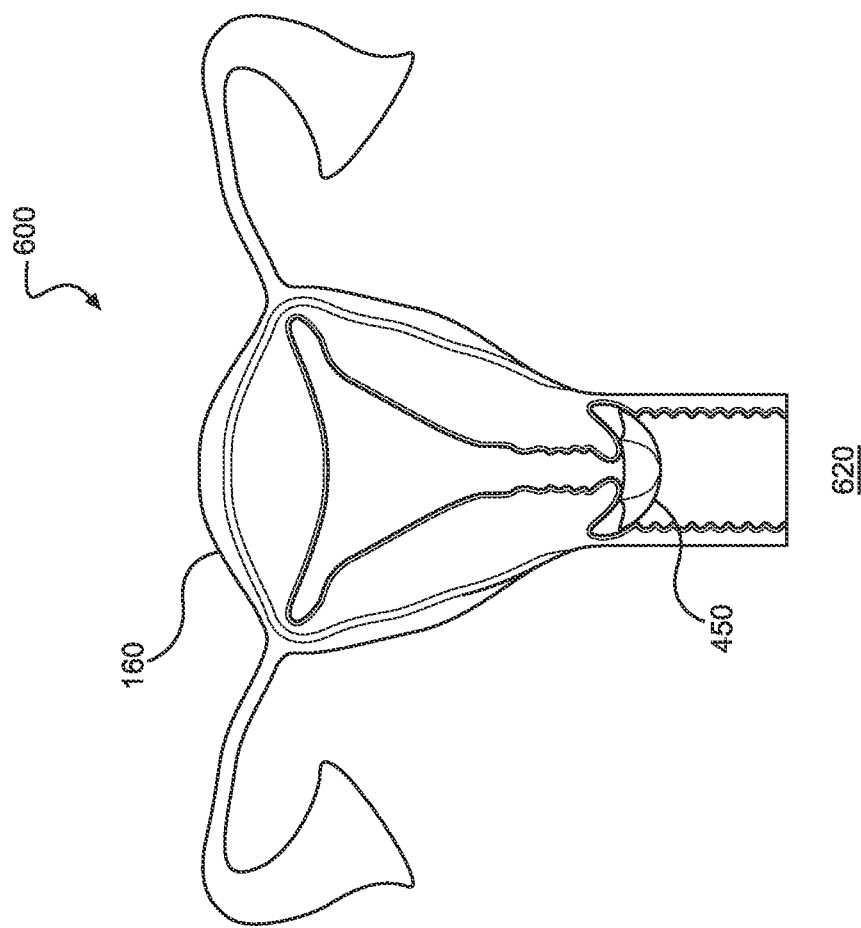
FIG. 6A and FIG. 6B are illustrations of exemplary postpartum hemorrhage mitigation devices after being positioned within a uterine cavity, in accordance with some embodiments of the present technology.
Figure 6A:
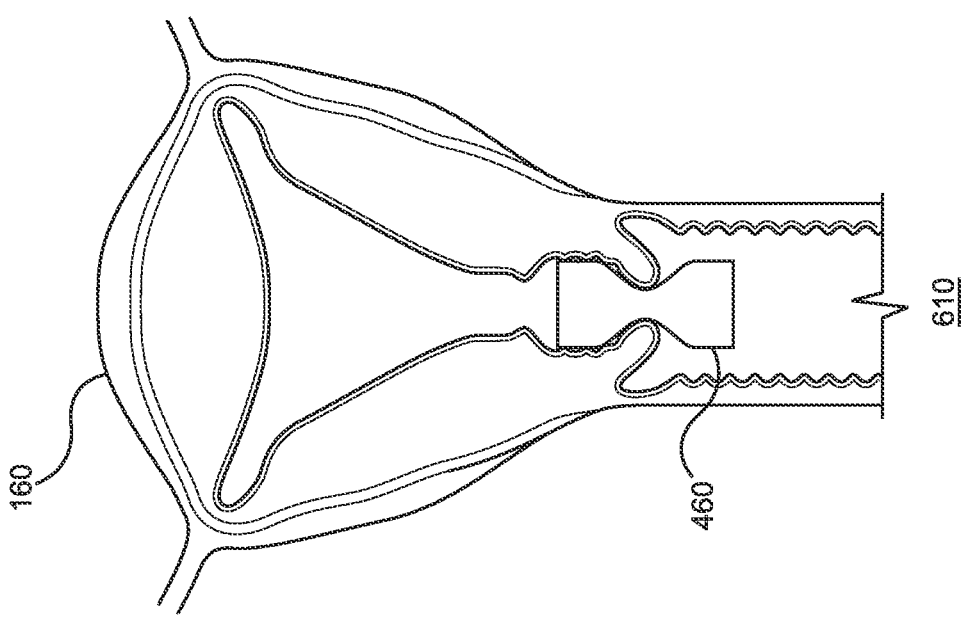

FIG. 6A and FIG. 6B are illustrations 600 of exemplary postpartum hemorrhage mitigation devices after being positioned within a uterine cavity, in accordance with some embodiments of the present technology. FIG. 6A and FIG. 6B show exemplary postpartum hemorrhage mitigation devices after being placed in position in the uterus, in contrast, FIG. 4 shows the postpartum hemorrhage mitigation devices before being positioned within in the uterus. For example, illustration 610 of FIG. 6A shows the hourglass shaped placement marker 460 positioned within the uterine cavity (e.g., uterine cavity 190) and a cervical canal (e.g., the cervical canal 180) of a mammal who recently gave birth either vaginally or via cesarean section. For example, the hourglass shaped placement marker 460 may be configured for movement along the suction line (not shown, e.g., suction line 130) for personalization of the postpartum hemorrhage mitigation device to a size of the uterus 160. For example, illustration 620 of FIG. 6B shows the collapsible anchoring mechanism 450 of FIG. 4 shown in the open configuration positioned covering a cervical canal (e.g., the cervical canal 180) of a mammal who recently gave birth either vaginally or via cesarean section.

FIG. 7 is an illustration of an exemplary postpartum hemorrhage mitigation device 700 before being positioned within a uterine cavity including a tapered catheter tip 715 to attach to the suction line, in accordance with some embodiments of the present technology. For example, illustration 710 of FIG. 7 shows the shape of a tapered catheter tip 715 including ridges (now shown) to attach to the suction line (not shown, e.g., the suction line 130). For example, the tapered catheter tip 715, which tapers on the proximal tip 105 that adds thickness and push-ability allowing ease of placement of the postpartum hemorrhage mitigation device 700 into a desired position. For example, the proximal tip 105 of the flexible tube further comprises a semi-ridged end 720, the semi-ridged end 720 being configured for steerability and push-ability of the postpartum hemorrhage mitigation device 700.

Figure 8:
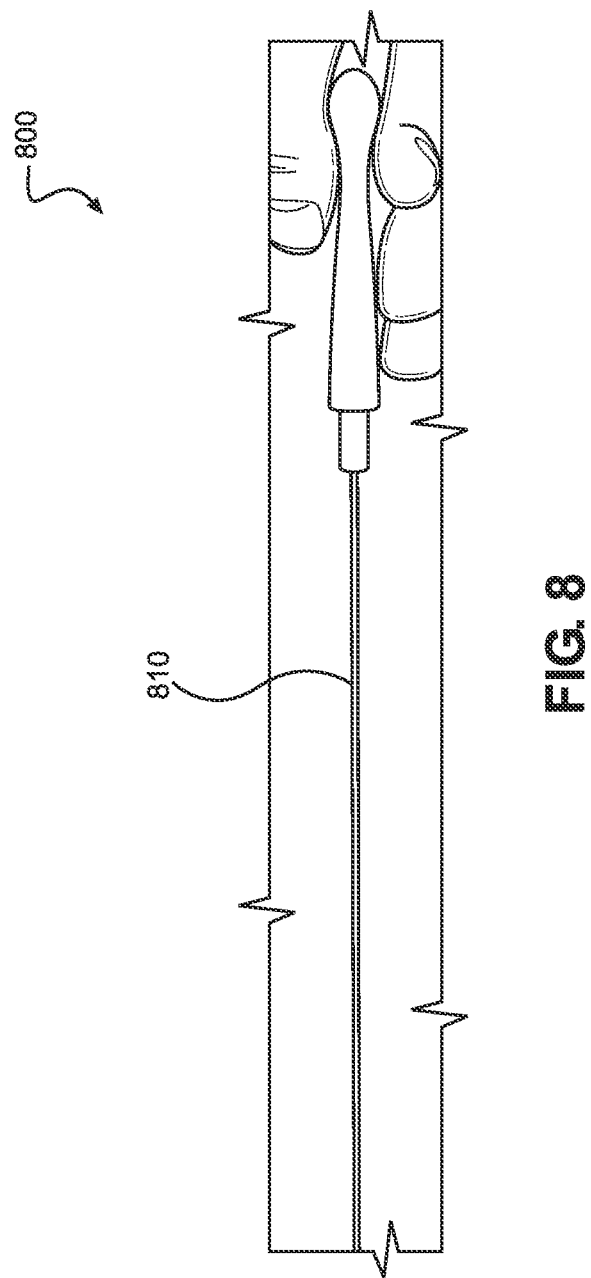
FIG. 8 is an illustration of an exemplary stylet for proper positioning of a postpartum hemorrhage mitigation device within the uterus including a tapered tip to attach to the suction line, in accordance with some embodiments of the present technology.

FIG. 8 is an illustration 800 of an exemplary stylet 810 for proper positioning of a postpartum hemorrhage mitigation device within the uterus including a tapered tip to attach to the suction line, in accordance with some embodiments of the present technology. For example, FIG. 8 shows the stylet 810 attached to an exemplary postpartum hemorrhage mitigation device for proper positioning of the postpartum hemorrhage mitigation device. For example, the stylet 810 may be a small, malleable plastic-coated metal rod that may be placed inside a suction line to reinforce or pre-shape the lumen of the tube to aid in directing the suction line towards the uterus. In some instances a guidewire (e.g., stylet 810) may be used to ease proper positioning of a postpartum hemorrhage mitigation device. For instance, the guidewire (e.g., stylet 810) may be used to properly position an anchoring mechanism in the uterus of a female woman who recently gave birth either vaginally or via cesarean section. For example, the guidewire (e.g., stylet 810) may comprise a malleable plastic-coated metal rod placed inside the at least one lumen to reinforce the at least one lumen, the malleable plastic-coated metal rod being configured for aiding directing of the suction line 130 towards the uterus 160.

In some embodiments, the guidewire may be used to guide the anchoring mechanism 120, and the suction line 130 of the postpartum hemorrhage mitigation device 100 into place during insertion of the postpartum hemorrhage mitigation device 100 within the uterine cavity 190.

Figure 9:
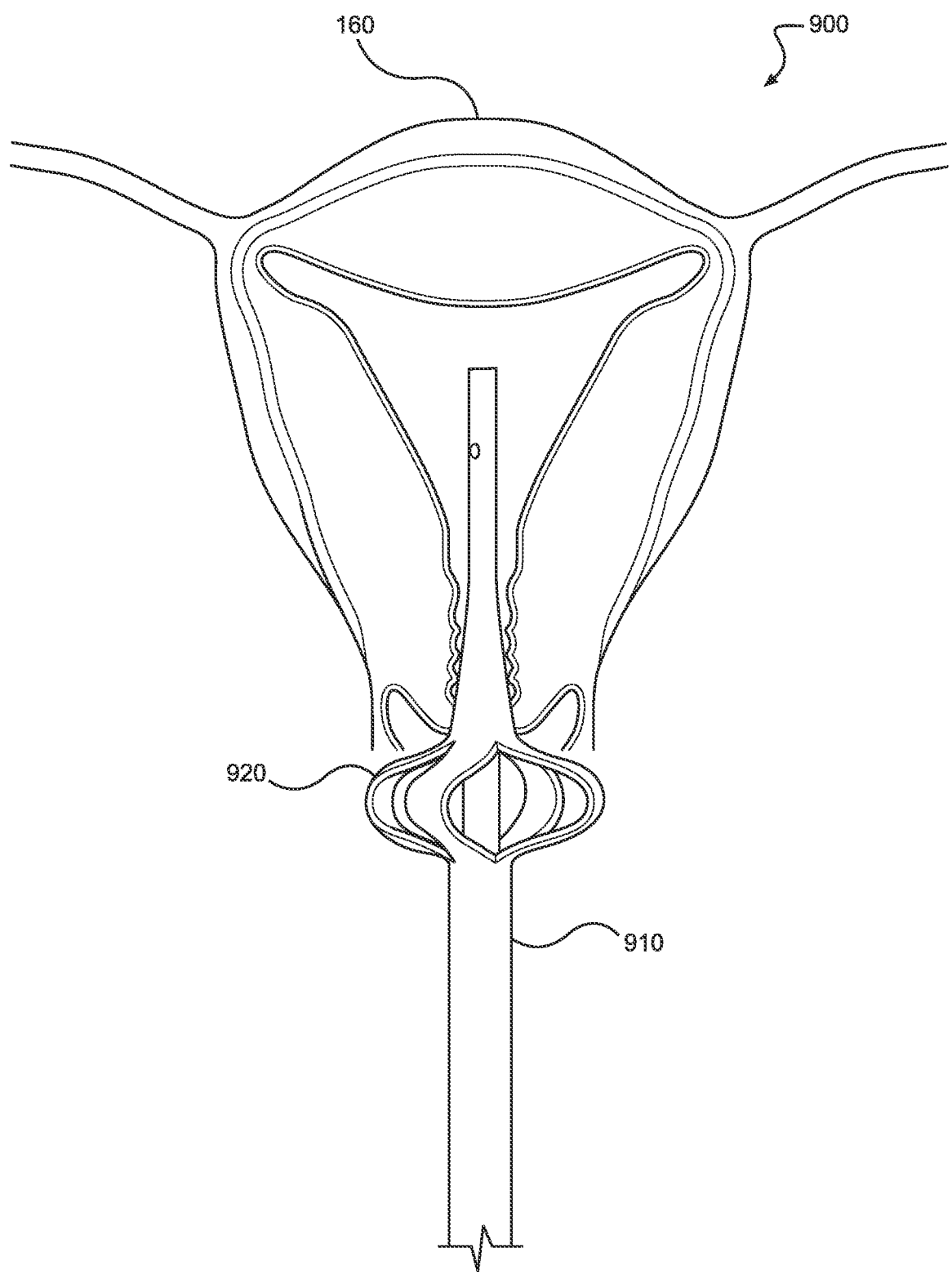
FIG. 9 is an illustration of an exemplary Malecot "flower" design used as an anchoring mechanism for a postpartum hemorrhage mitigation device within the vagina, in accordance with some embodiments of the present technology.

FIG. 9 is an illustration 900 of an exemplary Malecot "flower" design anchoring mechanism 920 used as an anchoring mechanism for a postpartum hemorrhage mitigation device 910 within the vagina, in accordance with some embodiments of the present technology. For example, illustration 900 of FIG. 9 shows an exemplary anchoring mechanism (e.g., anchoring mechanism 120 of FIG. 1 and anchoring mechanism 450 of FIG. 4) for a postpartum hemorrhage mitigation device 910 within the uterus 160. For example, the anchoring mechanism may use a Malecot "flower" design anchoring mechanism 920 that anchors the postpartum hemorrhage mitigation device 910 in the vagina of a woman after birth either vaginally or via cesarean section.

FIG. 10 is an illustration 1000 of an exemplary collapsible anchoring mechanism 450 for a postpartum hemorrhage mitigation device within the uterus, in accordance with some embodiments of the present technology. For example, FIG. 10 shows the collapsible anchoring mechanism 450 is an umbrella configuration comprising a plurality of wings. For example, wing A and wing B in alternating fashion. For example, the exemplary collapsible anchoring mechanism 450 may include a plurality of wings that alternate (e.g., wing A, wing B, wing A, wing B, wing A) and may be made of different materials such as solid material or mesh. Furthermore, in some embodiments a wing may be absent from the exemplary collapsible anchoring mechanism 450.

While this technology is susceptible of embodiments in many different forms, there is shown in the drawings and has been described in detail several specific embodiments with the understanding that the present disclosure is to be considered as an exemplification of the principles of the technology and is not intended to limit the technology to the embodiments illustrated.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer, or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. Exemplary embodiments were chosen and described in order to best explain the principles of the present disclosure and its practical application, and to enable others of ordinary skill in the art to understand the present disclosure for various embodiments with various modifications as are suited to the particular use contemplated.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A postpartum hemorrhage mitigation device comprising:
    a flexible tube comprising:
        a distal end;
        a proximal tip, the proximal tip comprising a suction line extension being configured for placement in a uterine cavity of a uterus after childbirth either vaginally or via cesarean section;
        a tube center of the flexible tube; and
        at least one lumen around the tube center, the at least one lumen comprising a suction line, the suction line being in communication with a source of negative pressure and the suction line extension, the suction line extension being configured for applying the negative pressure to the uterine cavity using the source of the negative pressure thereby causing mechanical hemostasis of bleeding blood vessels of a uterine wall of the uterine cavity;
        a placement marker, the placement marker being configured for movement along the suction line extension for personalization of the postpartum hemorrhage mitigation device to a size of the uterus, the placement marker covering one or more ports; and
        an anchoring mechanism being proximate to the suction line extension along the flexible tube, the anchoring mechanism being configured for maintaining the suction line extension in a desired position within the uterine cavity.

2. The postpartum hemorrhage mitigation device of claim 1, wherein the suction line extension further comprises one or more ports, the one or more ports being configured for drawing blood and other bodily fluids into the suction line extension from the bleeding blood vessels of the uterus.

3. The postpartum hemorrhage mitigation device of claim 2, wherein at least one of the suction line extension and the suction line comprise volumetric indications, the volumetric indications being configured for measurement of a volume of blood within the suction line extension and the suction line for quantifying blood loss from the bleeding blood vessels of the uterus for a clinician to evaluate postpartum hemorrhaging.

4. The postpartum hemorrhage mitigation device of claim 2, wherein the one or more ports comprise a plurality of ports, the plurality of ports comprising at least one of round pores, slits, and oval pores.

5. The postpartum hemorrhage mitigation device of claim 2, wherein the one or more ports comprise suction ports, the suction ports being positioned in a one-hundred-and-eighty-degree spiral configuration around the tube center.

6. The postpartum hemorrhage mitigation device of claim 5, wherein the at least one lumen comprises a plurality of lumens; and wherein the at least one lumen further comprises a guidewire.

7. The postpartum hemorrhage mitigation device of claim 6, wherein the guidewire comprises a malleable plastic-coated metal rod placed inside the at least one lumen to reinforce the at least one lumen, the malleable plastic-coated metal rod being configured for aiding directing of the suction line towards the uterus.

8. The postpartum hemorrhage mitigation device of claim 1, wherein the suction line comprises a semi-flexible catheter.

9. The postpartum hemorrhage mitigation device of claim 1, wherein the proximal tip of the flexible tube further comprises a semi-ridged end, the semi-ridged end being configured for steerability and push-ability of the postpartum hemorrhage mitigation device.

10. The postpartum hemorrhage mitigation device of claim 1, wherein the placement marker is an hourglass shaped placement marker, the hourglass shaped placement marker being configured for movement along the suction line for personalization of the postpartum hemorrhage mitigation device to a size of the uterus.

11. The postpartum hemorrhage mitigation device of claim 10, wherein the hourglass shaped placement marker covers one or more ports.

12. The postpartum hemorrhage mitigation device of claim 1, wherein the anchoring mechanism is a wavy placement anchor.

13. The postpartum hemorrhage mitigation device of claim 1, wherein the at least one lumen comprises a hydrophilic coating, the hydrophilic coating providing compatibility with bodily fluids and reducing friction of the at least one lumen.

14. A postpartum hemorrhage mitigation device comprising:
a flexible tube comprising:
a distal end;
a proximal tip, the proximal tip comprising a suction line extension being configured for placement in a uterine cavity of a uterus after childbirth either vaginally or via cesarean section, the suction line extension comprising one or more ports, the one or more ports being configured for drawing blood and other bodily fluids into the suction line extension from bleeding blood vessels of a uterine wall of the uterine cavity, the one or more ports comprising suction ports, the suction ports being positioned in a one-hundred-and-eighty-degree spiral configuration around a tube center of the flexible tube, the one-hundred-and-eighty-degree spiral configuration preventing blockage of all of the suction ports;
wherein the suction line extension further comprises volumetric indications, the volumetric indications being configured for measurement of a volume of blood within the suction line extension and the suction line for quantifying blood loss from the bleeding blood vessels for a clinician to evaluate postpartum hemorrhaging;
a placement marker, the placement marker being configured for movement along the suction line extension for personalization of the postpartum hemorrhage mitigation device to a size of the uterus, the placement marker covering the one or more ports; and
at least one lumen around the tube center, the at least one lumen comprising a suction line, the suction line being in communication with a source of negative pressure and the suction line extension, the suction line extension being configured for applying the negative pressure to the uterine cavity using the source of the negative pressure thereby causing mechanical hemostasis of the bleeding blood vessels of the uterine wall of the uterine cavity; and
an anchoring mechanism being proximate to the suction line extension along the flexible tube, the anchoring mechanism being configured for maintaining the suction line extension in a desired position within the uterine cavity.

15. A postpartum hemorrhage mitigation device comprising:
a flexible tube comprising:
a distal end;
a proximal tip, the proximal tip comprising a suction line extension being configured for placement in a uterine cavity of a uterus after childbirth either vaginally or via cesarean section, the suction line extension comprising one or more ports, the one or more ports being configured for drawing blood and other bodily fluids into the suction line extension from bleeding blood vessels of a uterine wall of the uterine cavity, the one or more ports comprising suction ports, the suction ports being positioned in a one-hundred-and-eighty-degree spiral configuration around a tube center of the flexible tube, the one-hundred-and-eighty-degree spiral configuration preventing blockage of all of the suction ports;
a placement marker, the placement marker being configured for movement along the suction line extension for personalization of the postpartum hemorrhage mitigation device to a size of the uterus, the placement marker covering the one or more ports;
at least one lumen around the tube center, the at least one lumen comprising a suction line, the suction line being in communication with a source of negative pressure and the suction line extension, the suction line extension being configured for applying the negative pressure to the uterine cavity using the source of the negative pressure thereby causing mechanical hemostasis of the bleeding blood vessels of the uterine wall of the uterine cavity; and
an anchoring mechanism being proximate to the suction line extension along the flexible tube, the anchoring mechanism being configured for maintaining the suction line extension in a desired position within the uterine cavity.

* * * * *